United States Patent [19]

Lavender

[11] Patent Number: 5,147,340
[45] Date of Patent: Sep. 15, 1992

[54] TWO-PIECE OSTOMY APPLIANCE

[75] Inventor: Michael R. Lavender, Round Lake Beach, Ill.

[73] Assignee: Hollister Incorporated, Libertyville, Ill.

[21] Appl. No.: 686,397

[22] Filed: Apr. 18, 1991

[51] Int. Cl.⁵ .................................. A61F 5/44
[52] U.S. Cl. ..................... 604/344; 604/332; 604/336; 604/338; 604/339; 604/342
[58] Field of Search ............... 604/332, 336, 338, 339, 604/340, 341, 342, 344

[56] References Cited

U.S. PATENT DOCUMENTS

| | | | |
|---|---|---|---|
| 4,834,731 | 5/1989 | Nowak et al. | 604/339 |
| 4,889,534 | 12/1989 | Mohiuddin et al. | 604/339 |
| 4,973,323 | 11/1990 | Kaczmarek et al. | 604/339 |

Primary Examiner—Randall L. Green
Assistant Examiner—A. Paul Zuttarelli
Attorney, Agent, or Firm—Tilton Fallon Lungmus

[57] ABSTRACT

A two-piece ostomy appliance in the form of a collection pouch and an adhesive faceplate respectively equipped with coupling rings for latching the two parts together. The coupling rings are relatively large and the pouch coupling ring has attached thereto a peristomal barrier ring of soft, deformable, skin-contacting sealant material extending radially inwardly from the pouch coupling ring and defining a stoma-receiving opening.

5 Claims, 1 Drawing Sheet

TWO-PIECE OSTOMY APPLIANCE

BACKGROUND AND SUMMARY

In a conventional two-piece ostomy appliance, the plastic coupling rings of a pouch and faceplate form the dual functions of mechanically securing the parts together and forming a fluid-tight seal to prevent the escape of exudate and gases The second of these functions, in particular, requires that the mating rings be precisely matched, and that they not be scratched, deformed, or otherwise damaged in handling, if problems of leakage are to be avoided. Even when care is taken to avoid such damage and security is achieved, the needs of ostomates may not be completely met by current products That is often the case even where the faceplates of current two-piece products are used with protective skin barrier rings that sealingly contact the peristomal skin surfaces and are intended to prevent leakage and protect the skin from the excoriating effects of exudate contact.

Some two-piece appliances are objectionable because they are not low enough in "profile" to allow concealment of their use beneath a patient's clothing. Others fail to provide sufficient tactile feedback to signal the user when a fluid-tight seal has been formed. Another typical problem is that the close proximity of the faceplate's skin barrier ring to the stoma makes cleaning of the peristomal area difficult when the pouch is removed and the stoma is exposed. Furthermore, skin barrier materials of ostomy appliances are ordinarily of compromise or all-purpose formulations expected to be used with stomas located at any of a variety of sites such as the ileum, the descending colon, or the ureter, even though such a composition may not be ideally formulated for the particular location involved. What is needed is an appliance skin barrier that is matched to the solubility characteristics of the exudate from a specific location for a given patient, thereby minimizing barrier erosion and enabling predictable weartime.

Accordingly, it is an object of this invention to provide a two-piece ostomy appliance that overcomes the aforementioned shortcomings of existing appliances. Specifically, the appliance of this invention utilizes coupling rings that perform only a mechanical latching function, not a sealing function, and therefore need not be precisely formed and matched to provide a liquid-tight seal. Slight surface imperfections in the coupling rings occurring during manufacture or use do not compromise the sealing effectiveness of the appliance because the rings are needed only to provide a secure mechanical interconnection.

Since the pouch's barrier ring is held in place against the wearer's skin by the mechanical latching between the coupling rings and the surrounding adhesive attachment of the faceplate to the patient, a sealant composition of reduced tack, or even no tack, may be used, thereby reducing one cause of skin stripping and irritation. Also, since the barrier ring is mounted upon the pouch rather than the faceplate, the arrangement allows multiple barrier compositions to be used with the same faceplate, thereby matching the right barrier to a specific user need. Such matching minimizes barrier erosion and makes weartime more predictable than with conventional appliances.

Since the barrier is provided as part of the pouch subassembly, removal of the pouch results in exposure of a substantial peristomal area even though the faceplate remains in place. Such an arrangement makes cleaning of the site easier and more effective. The arrangement also lends itself to having a lower profile than existing systems, thereby increasing the likelihood that the user's medical condition will not be unintentionally disclosed by unsightly bulges in clothing. The assembly tends to produce an audible and tactile click when latched so that attachment to the skin of the pouch barrier ring may be tactily perceived, thereby enhancing the perceived security of the device.

Briefly, the appliance takes the form of a collection pouch with a flexible plastic first coupling ring secured to its side wall about an opening formed therein, and a faceplate having a second coupling ring of flexible plastic adapted to latch with the first coupling ring of the pouch. The faceplate includes annular adhesive attaching means extending radially outwardly from the second coupling ring for adhesively engaging a wearer's skin.

A particularly important feature is the provision of a pouch barrier ring of soft, deformable, skin-contacting sealant material, preferably an adhesive material having both wet and dry tack, secured to the first coupling ring, that is, the pouch coupling ring. The pouch barrier ring extends inwardly from that coupling ring and has an outside diameter smaller than the opening of the adhesive attachment means of the faceplate. Therefore, the pouch barrier ring makes sealing contact with peristomal skin surfaces within the area circumscribed by both coupling rings and by the adhesive attachment means of the faceplate, when the appliance is worn.

Other features, advantages, and objects will be appear from the specification and drawings.

DRAWINGS

DETAILED DESCRIPTION OF PREFERRED EMBODIMENTS

Figure 1:
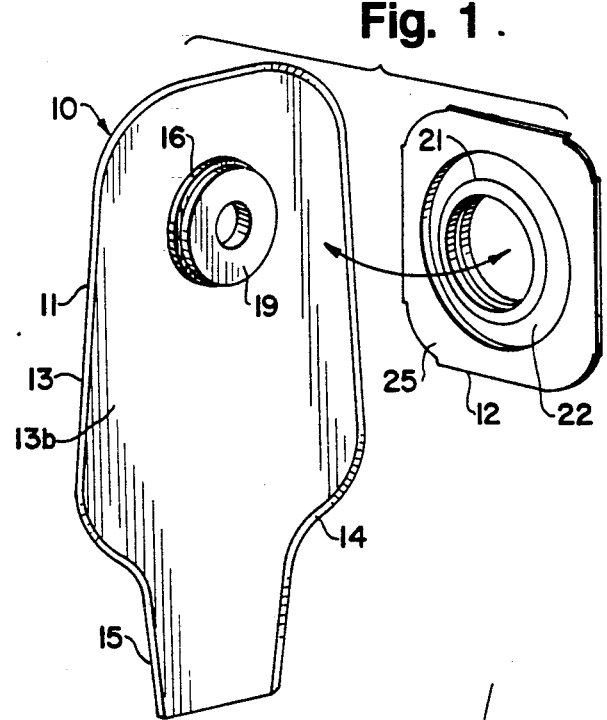
FIG. 1 is a perspective view of a pouch and faceplate embodying the invention.
Figure 2:
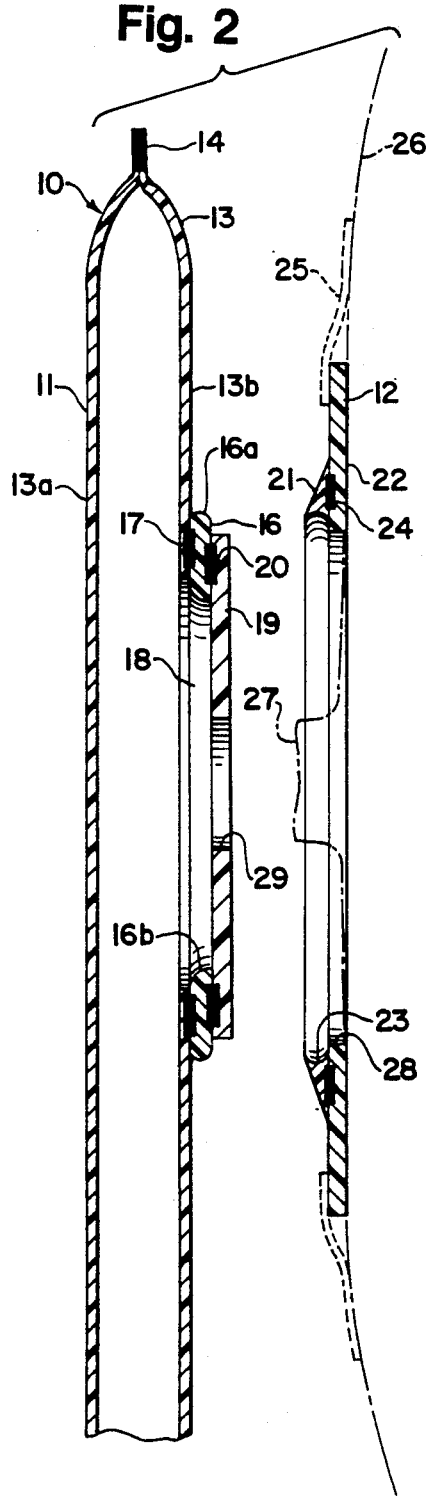
FIG. 2 is a vertical sectional view of the pouch and faceplate in disconnected condition.
Figure 3:
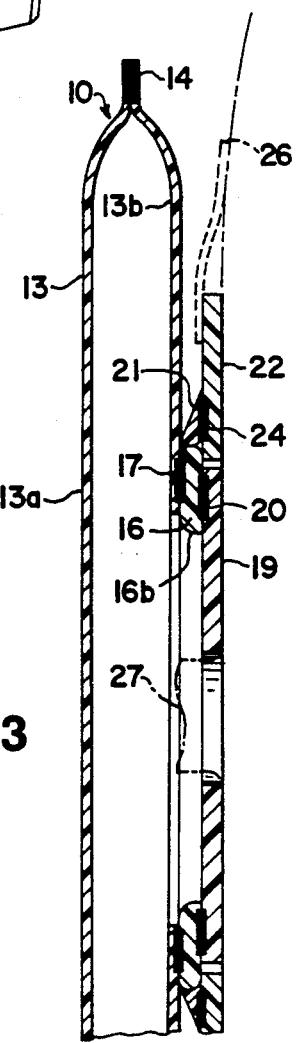
FIG. 3 is a sectional view of the pouch and faceplate coupled together.

Referring to the embodiment shown in FIGS. 1-3, the numeral 10 generally designates a two-piece appliance comprising a pouch subassembly 11 and a faceplate subassembly 12. The pouch subassembly includes a collection pouch 13 which may be formed of two panels 13a and 13b of thermoplastic film joined together by a peripheral zone of heat sealing 14 and terminating in an open neck portion 15 at the pouch's lower end. Where such a neck portion is provided, a suitable clamp, such as the clamp disclosed in U.S. Pat. No. 3,523,534, may be used to maintain the pouch's lower end in closed condition. Alternatively, neck portion 15 may be omitted entirely and the heat-sealing zone may extend about the full periphery of the pouch.

A first coupling ring 16 is secured to one wall 13b of the pouch by heat sealing at 17 or by any other suitable means. The ring is composed of a flexible plastic material and, while low-density polyethylene has been found particularly effective, other materials having similar properties may be used. The ring is relatively flat in profile (FIG. 2) and has a rounded outer peripheral edge 16a and an inner edge 16b defining a relatively large opening 18.

A pouch barrier ring 19 is secured to the face of the first coupling ring and extends radially inwardly therefrom. Like the coupling ring, pouch barrier ring 19 may be relatively thin so that the entire pouch subassembly retains a low profile. Pouch barrier ring 19 is planar as shown but is readily deformable, being formed of soft, deformable or compressible, polymeric material One such material may be of moisture-absorbent, skin-adherent barrier composition formulated from a mixture of elastomers and hydrocolloids and having both wet and dry tack. For example, polyisobutylene may be employed as one elastomeric ingredient. Since polyisobutylene cannot itself be chemically or physically cross-linked, it is necessary to include a cross-linking elastomeric resin in the formulation. Cross-linkable resins which blend with polyisobutylene to form a continuous elastomeric phase include the copolymer resins formed from ethylene and vinyl acetate. Suitable formulations of EVA resins with polyisobutylene are disclosed in U.S. Pat. Nos. 4,477,325 and 4,738,257. For purposes of the present invention, from 40 to 60 parts of vinyl acetate may be copolymerized with from 60 to 40 parts by weight of ethylene; however, the exact proportions are not critical.

To provide for fluid absorption, the barrier material may contain a relatively high proportion of hydrocolloid, and also a super-absorbent type hydrocolloid. Super-absorbents can be formed from starch and acrylonitrile, the starch, either gelatinized or in granular form, being reacted with the acrylonitrile under alkaline conditions. Synthetic super-absorbents may also be utilized, such as sodium polyacrylates.

The hydrocolloids which may be employed alone or in combination with the super-absorbent material include pectin, carboxymethylcellulose, such as sodium CMC, karaya, gelatin, guar, etc. The hydrocolloid mixture may include both natural vegetable hydrocolloid gums and synethetic hydrocolloids, for example, a mixture of pectin and sodium CMC has been found particularly suitable, especially when used in admixture with a super-absorbent such as sodium polyacrylate.

Other skin barrier formulations, or variations of such formulations, are disclosed in the aforementioned patents and are also known in the art. Any suitable barrier composition which is soft, pliant, hydrophillic, and has both wet and dry tack may be used. The pouch barrier ring is preferably heat sealed to the first coupling ring 16 as indicated by heat seal 20, although other means for securely attaching the two elements together may be provided.

While skin barrier formulations having adhesive properties are highly advantageous, the fact that the pouch barrier ring 19 may be compressed against the skin (by the coaction of coupling rings 16, 21 and the adhesive attachment ring 22 of the faceplate) also permits the utilization of a soft, compressible, elastomeric sealant material that is non-adhesive or tack-free. As long as the compliant barrier ring 19 forms a liquid- and gas-tight seal with the peristomal skin surfaces, the absence of adhesive contact with the skin may even be beneficial. For example, polyurethane elastomers that are hydrophilic are believed particularly suitable because their hydrophilicity allows moisture to wick away from the skin, thereby preventing skin maceration, and the relatively high vapor transmission characteristics of such materials permit the diffusion of enough oxygen and carbon dioxide to vent the peristomal skin while at the same time acting as an effective seal against the escape of flatus. Such a ring may effect a tight seal against the skin because of its conformability and compressibilty, even though lacking in adhesive properties. Since such a ring is tack-free, problems of skin trauma are eliminated or greatly reduced even though pouches equipped with barrier rings of such material may be frequently attached and removed.

The faceplate subassembly 12 comprises a second coupling ring 21 adapted to mate with the first coupling ring 16 and adhesive attachment means 22 secured to the second coupling ring for removably securing subassembly 12 to a wearer's skin. In the embodiment illustrated, coupling ring 21 is larger than ring 16 and has an inwardly facing annular channel 23 for receiving the rounded outer periphery 16a of pouch ring 16. The faceplate ring 21 may be formed of the same flexible and slightly resilient material as pouch ring 16. The fact that the two rings are coplanar when coupled together is believed highly advantageous because it results in an assembly of a relatively thin or flat profile; also, the snap fit between the rings, and their coplanar relationship when fully latched, give tactile feedback to the user assuring him/her when the parts are fully latched together. It is to be understood, however, that coupling rings of other shapes and different modes of mechanical interconnection may be provided. What is important is that when coupled together, the rings produce a secure but releasable mechanical connection between the two subassemblies.

In contrast to prior two-piece appliances, the appliance 10 does not rely upon coupling rings 16 and 21 to produce a fluid- and gas-tight seal between the parts. All that is required of the coupling rings 16 and 21 is that they produce a secure and reliable mechanical interlock and, preferably, that they place the deformable barrier ring 19 under compressive load (especially important where a tack-free barrier composition is used). It is also preferred that the coupling rings interlock in a way that generates some tactile feedback and produces an assembly of low profile. The design constraints in the development of prior constructions that arise where coupling rings must perform a sealing function as well as a latching function are not present here because the sealing functions is performed by another element, namely, the barrier ring 19 that extends radially inwardly from the pouch ring 16 and forms a fluid-tight seal with the skin surfaces immediately surrounding the stoma.

The adhesive attachment means of the faceplate may take the form of an outer faceplate ring 22 of skin barrier material having sufficient adhesive properties to securely affix the faceplate to a wearer's skin. Alternatively, the attaching means may take the form of a porous or microporous fabric ring or patch having its skin-contacting face coated with a suitable medical-grade pressure-sensitive adhesive. An adhesive-coated, non-woven, microporous material, as disclosed in U.S. Pat. No. 4,213,458, is believed particularly effective. The faceplate ring 22 is preferably secured to coupling ring 21 by means of a heat seal 24, but other sealing means, such as an adhesive connection, may be used.

In the embodiment illustrated in the drawings, the means for securing the faceplate to the wearer includes both faceplate barrier ring 22 and an outer framing ring or patch 25 of microporous material The patch 25 is optional, as indicated by broken lines in FIGS. 2 and 3 and, when used, is preferably adhesively secured to the outer surface of ring 22 facing away from the patient and to the peristomal skin surfaces surrounding the barrier ring 22.

In FIGS. 2 and 3, the outline of a wearer's body is indicated in phantom at 26 and the stoma at 27. When the faceplate 12 is properly secured to a patient, stoma 27 is centered within the relatively large opening 28 of the faceplate. A substantial area of skin surface is exposed about the stoma, thereby facilitating the cleaning of the peristomal surfaces without the necessity of removing the faceplate itself. The substantial radial spacing between the stoma and the latching surface 23 of the faceplate coupling ring 21 is also advantageous because it eliminates or at least reduces the possibility of exudate contacting such latching surfaces and requiring cleaning of the faceplate coupling ring before attachment of a pouch.

Prior to attachment of the pouch subassembly, the opening 29 of the barrier ring 19 is sized to accommodate the stoma. Coupling ring 16 is then simply attached to faceplate coupling ring 21, bringing the barrier ring 19 into sealing contact with the peristomal skin surfaces. Because the barrier ring completely surrounds the stoma and is interposed between the stoma and the adhesive attachment means 22 of the faceplate, the faceplate, and the adhesive securing that faceplate to the patient, are fully protected against exudate contact.

Since the barrier ring essentially performs only a sealing function and is not relied upon to secure the pouch assembly to the patient, the composition of the barrier may be varied to meet specific user needs. Those needs vary depending on the location of the ostomy. By matching the barrier composition to the needs of a user, erosion of the barrier may be minimized and weartime made more predictable.

While in the foregoing, I have disclosed an embodiment of the invention in considerable detail for purposes of illustration, it will be understood by those skilled in the art that many of these details may be varied without departing from the spirit and scope of the invention.

I claim:

1. An ostomy appliance comprising a collection pouch having a side wall with an opening therein; a flexible plastic first coupling ring secured to said side wall about said opening; a faceplate having a second coupling ring of flexible plastic adapted to latch with said first coupling ring; said forceplate including annular adhesive attachment means defining an opening and extending radially outwardly from said second coupling ring for adhesively engaging a wearer's skin; wherein the improvement comprises a pouch barrier ring of soft, compressible, sealant material secured to said first coupling ring; said pouch barrier ring having an outside diameter smaller than said opening of said adhesive attachment means and extending radially inwardly from said first coupling ring for sealing contact with surfaces of a wearer's skin within the area circumscribed by both of said coupling rings when said appliance is worn.

2. The appliance of claim 1 in which said soft, compressible, sealant material has both wet and dry tack.

3. The appliance of claim 1 in which said soft, compressible, sealant material is tack-free.

4. The appliance of claims 1, 2, or 3 in which said adhesive attachment means comprising a faceplate barrier ring of soft, deformable, skin barrier material having wet and dry tack.

5. The appliance of claim 4 in which said adhesive attachment means also includes a soft, flexible, microporous patch secured to said faceplate barrier ring and extending radially outwardly therefrom; said microporous patch having an adhesive surface for adhesive contact with a wearer's skin.

* * * * *